United States Patent
Kelso et al.

(10) Patent No.: US 7,764,361 B2
(45) Date of Patent: Jul. 27, 2010

(54) SYSTEMS AND METHODS TO ANALYZE MULTIPLEXED BEAD-BASED ASSAYS USING BACKSCATTERED LIGHT

(75) Inventors: David M. Kelso, Wilmette, IL (US); Abhishek Mathur, Newbury Park, CA (US)

(73) Assignee: Northwestern University, Evanston, IL (US)

( * ) Notice: Subject to any disclaimer, the term of this patent is extended or adjusted under 35 U.S.C. 154(b) by 479 days.

(21) Appl. No.: 11/829,631

(22) Filed: Jul. 27, 2007

(65) Prior Publication Data

US 2008/0246968 A1   Oct. 9, 2008

Related U.S. Application Data

(60) Provisional application No. 60/833,581, filed on Jul. 27, 2006.

(51) Int. Cl.
*G01J 3/30* (2006.01)
(52) U.S. Cl. ............ 356/73; 356/417; 356/342
(58) Field of Classification Search ........... 356/73, 356/417, 342
See application file for complete search history.

(56) References Cited

U.S. PATENT DOCUMENTS

| | | | |
|---|---|---|---|
| 5,072,382 A | 12/1991 | Kamentsky | |
| 5,689,317 A | 11/1997 | Miller | |
| 5,852,498 A * | 12/1998 | Youvan et al. | 356/417 |
| 5,885,840 A | 3/1999 | Kamentsky et al. | |
| 5,943,129 A | 8/1999 | Hoyt et al. | |
| 5,981,180 A | 11/1999 | Chandler et al. | |
| 6,274,323 B1 | 8/2001 | Bruchez et al. | |
| 6,500,622 B2 | 12/2002 | Bruchez, Jr. et al. | |
| 6,602,671 B1 | 8/2003 | Bawendi | |
| 6,656,683 B1 | 12/2003 | Reuben et al. | |
| 6,734,420 B2 | 5/2004 | Empedocles et al. | |
| 6,759,235 B2 | 7/2004 | Empedocles et al. | |
| 6,916,661 B2 | 7/2005 | Chandler et al. | |
| RE38,817 E | 10/2005 | Slettnes | |
| 6,970,246 B2 | 11/2005 | Hansen | |
| 2001/0007496 A1 * | 7/2001 | Modlin et al. | 356/73 |
| 2003/0014135 A1 | 1/2003 | Moulios | |
| 2003/0148544 A1 | 8/2003 | Nie et al. | |
| 2004/0033359 A1 | 2/2004 | Bawendi et al. | |
| 2006/0170907 A1 * | 8/2006 | Tuschel | 356/73 |
| 2009/0147242 A1 * | 6/2009 | Treado et al. | 356/73 |

OTHER PUBLICATIONS

Kamentsky et al., "Micro-Based Multiparameter Laser Scanning Cytometer Yielding Data Comparable to Flow Cytometry Data" 1991 Cytometry 12, 381-387.

Han et al., "Quantum-dot-tagged microbeads for multiplexed optical coding of biomolecules" 2001 Nature Biotechnology 19(7) 631-5.

(Continued)

*Primary Examiner*—Kara E Geisel
(74) *Attorney, Agent, or Firm*—Casimir & Jones, S.C.

(57) ABSTRACT

This invention relates to a system and method related to an epifluorescence microscope based optical system equipped with a tunable filter to localize microspheres in bead-based assays based on a back-scattered light (also known as reflected light) image. A common optical path for reflected and emitted luminescence in conjunction with a tunable filter negates the requirement of an additional sensor employed in existing technologies for localizing microspheres based on light scatter measurements.

11 Claims, 2 Drawing Sheets

OTHER PUBLICATIONS

Beucher, "The Watershed Transformation Applied to Image Segmentation" 1992 Scanning Microscopy International.

Beucher and Meyer, "The Morphological Approach to Segmentation: The Watershed Transformation" 1993 Dougherty, E.R., editor Mathematical Morphology in Image Processing, New York, Basel, Hong Kong, Marchel Dekker, 433-482.

Stoll et al., "Protein Microarray Technology," 2002 Frontiers in Bioscience 7, c13-c32.

Dewildt et al., "Antibody Arrays for High-Throughput Screening of Antibody-Antigen Interactions" 2000 Nature Biotechnol. 18, 989-994.

Schaffitzel et al., "Ribosome Display: an In Vitro Method for Selection and Evolution of Antibodies From Libraries" 1999 J. Immunol. Methods 231, 119-135.

Uetz et al., "Systematic and large-scale two-hybrid screens" 2000 Curr Opin Microbiol 3(3):303-8.

* cited by examiner

SYSTEMS AND METHODS TO ANALYZE MULTIPLEXED BEAD-BASED ASSAYS USING BACKSCATTERED LIGHT

CROSS-REFERENCE TO RELATED APPLICATIONS

This application claims the benefit of U.S. Provisional Patent Application Ser. No. 60/833,581 filed Jul. 27, 2006, the entire disclosure of which is incorporated by reference.

STATEMENT OF GOVERNMENT RIGHTS

This invention was made with United States government support awarded by the following agencies: National Institute of Biomedical Imaging and Bioengineering, Award Number RO1EB001418.

FIELD OF THE INVENTION

The present invention relates generally to the field of microscopy. More particularly, this invention relates to apparatus, systems and methods for conducting microscopy studies using bead-based assays.

BACKGROUND OF THE INVENTION

Systems that acquire images of luminescently-labeled microspheres have proven useful for assays. In some such systems, images of assayed microspheres are acquired at multiple emission wavelengths. The luminescent spectral code and fluorescence from each microsphere can be read by superimposing the multispectral images of the same Field of View (FOV) after the application of an image segmentation algorithm. However, in this scheme, microspheres in each of the multispectral images need to be localized separately before the superimposition. The analysis is computationally intensive and the processing time increases proportionally with the increase in number of colors (i.e., wavelengths).

Another method involves localizing the positions of microspheres in an array using forward scatter measurements and then reading the luminescence at multiple wavelengths from those locations (Kamentsky et al, "Micro-Based Multiparameter Laser Scanning Cytometer Yielding Data Comparable to Flow Cytometry Data," *Cytometry* 12, 381-387 (1991); and U.S. Pat. Nos. 5,885,840 and 5,072,382). Several variations of this method have been proposed (see, for example, U.S. Pat. Nos. 6,970,246, 6,759,235, 6,656,683 and RE38,817). However, in all of these methods, the imaging apparatus requires a different sensor (such as a photomultiplier tube) to measure the forward scatter signal. While sensors measuring luminescence may be present on the same side of the specimen as the excitation source, the sensor measuring forward scatter is positioned on the opposite side of the specimen such as in Laser Scanning Cytometer (Compucyte, Inc.) (see, for example, Kamentsky et al., "Micro-Based Multiparameter Laser Scanning Cytometer Yielding Data Comparable to Flow Cytometry Data," *Cytomety* 12, 381-387 (1991); and U.S. Pat. No. 5,072,382). An imaging system with multiple sensors to image the same FOV is more susceptible to optical alignment problems and prone to errors in the signal measurements.

SUMMARY OF THE INVENTION

The present invention provides apparatus, systems and methods to luminescently identify spectrally coded beads in a sample and to quantify multiple target molecules immobilized on the beads, based on the analysis of high throughput multiplexed assays which employ spectrally coded beads, such as polymer microspheres. These microspheres may be coded with semiconductor nanocrystals (commonly known as Quantum Dots (QDs)), which have distinct emission wavelengths. Such high throughput screening (HTS) systems find their applications in protein interaction mapping, proteomics, functional genomics, drug development, immunodiagnostics, hybridoma-library and phage-library screening, and protein profiling of cells and tissues. Such systems have also been used in assaying a sample for target polynucleotides or corresponding amplification products.

Instead of the flow cytometric analysis such as one employed in the Luminex™ bead-based assay system with fluorescent dyes as spectral labels (see, for example, U.S. Pat. Nos. 5,981,180 and 6,916,661), the present invention uses an optical imaging system to acquire signal information from bead-based assays, including those that employ the QD labeled microspheres. In such assays, the microspheres can be tailored to produce a characteristic luminescent emission or signal by changing the composition and/or size of the semiconductor nanocrystals embedded therein.

One embodiment of the invention relates to an epifluorescence microscope based optical system equipped with a tunable filter to localize microspheres in bead-based assays based on a back-scattered light image (also known as reflected light image) and to read emission spectra from the microspheres. A common optical path for the reflected light and luminescent emission from the beads in conjunction with a tunable filter negates the requirement of an additional sensor employed in existing technologies for localizing microspheres based on light scatter measurements.

In addition to locating and identifying the luminescence emission of the beads, the present systems may be used to identify and quantify target molecules immobilized on the beads. In this embodiment, the systems may use target molecules having attached labels, wherein the labels emit a luminescent signal when excited by the excitation radiation. The labels may be, but are not limited to, fluorescent labels, phosphor labels, and/or scattering labels. Specific examples of labels that may be associated with the target molecules include fluorescent dyes, quantum dots and colloidal gold. The labels desirably have excitation wavelengths as well as emission wavelengths that overlap with the excitation wavelength band of the luminescently coded beads. For example, the excitation and emission wavelengths of the labels may overlap with the excitation wavelength band for the QDs used for labeling polymer microspheres. In this embodiment of the method, images acquired at emission wavelengths of the target molecules can be utilized for localizing the microspheres as well as for identifying and quantifying the target molecules. This reduces the number of images per FOV required for analysis, thereby reducing the imaging and analysis time, The system also allows for the utilization of uncoded or blank microbeads as assay platforms. An image analysis algorithm, which compensates for any small drift of microspheres in the array, may optionally be employed to improve the image.

In one embodiment, the present invention provides a single detector imaging system that includes a radiation source (e.g., an ultraviolet (UV) light source), that directs excitation radiation onto a sample; a sample platform for holding the sample; a tunable filter positioned in a common optical path for backscattered radiation reflected from the sample and luminescence radiation emitted by the sample; and a detector for detecting the radiation passed by the tunable filter. The tunable filter may be tuned to an excitation wavelength of the excitation radiation and to a plurality of luminescence emission wavelengths of the spectrally coded beads in the sample. In addition, the system may include an excitation filter positioned to the path of the excitation radiation to restrict the excitation radiation striking the sample to certain selected excitation wavelengths and a dichroic mirror disposed in the path of the excitation radiation, beyond the excitation filter, and in the common optical path of back-scattered radiation reflected from the sample and luminescence radiation emitted by the sample, to allow radiation passing through the excitation filter to be reflected by the dichroic mirror to the sample and back-scattered radiation to be transmitted by the dichroic mirror to the tunable filter.

The systems provided herein may be used in bead-based assay methods for locating and identifying spectrally coded beads in a sample. One embodiment of such a method includes the steps of directing excitation radiation (e.g., UV light) onto the beads in the sample, identifying the locations of the beads in the sample by detecting back-scattered radiation from the beads, and identifying the spectral code of each bead by detecting luminescent radiation emitted by each bead a plurality of emission wavelengths. In this method, the back-scattered radiation and the luminescence emissions from the beads, which share a common optical path, pass through a tunable filter prior to being detected by a radiation detector. In the case of the back-scattered radiation, the tunable filter is tuned to an excitation wavelength of the excitation radiation. In the case of the luminescence emission, the tunable filter is tuned sequentially through each of the plurality of emission wavelengths that make up the spectral codes for the beads.

In summary, systems and methods for performing faster and more robust bead-based assays have been developed. This set of systems and methods provides significant advantages over existing technologies in analyzing patient samples for a number of analytes, However, obvious variations can be made to it without departing from the spirit and the scope of the invention.

DETAILED DESCRIPTION OF THE PREFERRED EMBODIMENTS

To overcome the limitations of a multisensor imaging system, novel methods and systems have been developed in which back-scattered light (also known as 'reflected light') from beads in a sample in an FOV is utilized to localize the beads and emitted luminescence signal is read from the corresponding locations in the images at various emission wavelengths to determine the spectral code for each bead. The system, which does not require any additional sensor for measuring the reflected light signal, tunes a tunable filter to the excitation wavelength in order to detect back-scattered light, similar to detecting the emitted luminescence signal when the tuning filter is tuned to different emission wavelengths. The system helps to eliminate any calibration errors that occur due to misalignment problems in systems with multiple sensors. As used herein, the term "tunable filter" refers to any device that is capable of being tuned to selectively transmit radiation of different wavelengths. Thus, examples of tunable filters include, but are not limited to, tunable band pass filter or a wheel housing a plurality of fixed wavelength filters that may be placed in the path of the radiation and rotated.

In the following description, for purposes of explanation, numerous specific details are set forth to provide a thorough understanding of exemplary embodiments of the invention. It will be evident, however, to one skilled in the art that the invention may be practiced without these specific details. In other instances, well-known structures and devices are shown in block diagram form to facilitate description of the exemplary embodiments. For purposes of illustration only, the methods and systems will be described primarily in terms of a sample comprising polymer microspheres having QDs embedded therein and fluorescently-labeled target molecules immobilized thereon. The excitation source used in the illustrations is an UV light source. However, other types of luminescently-coded beads, target molecule labels and excitation sources may also be used.

Figure 1:
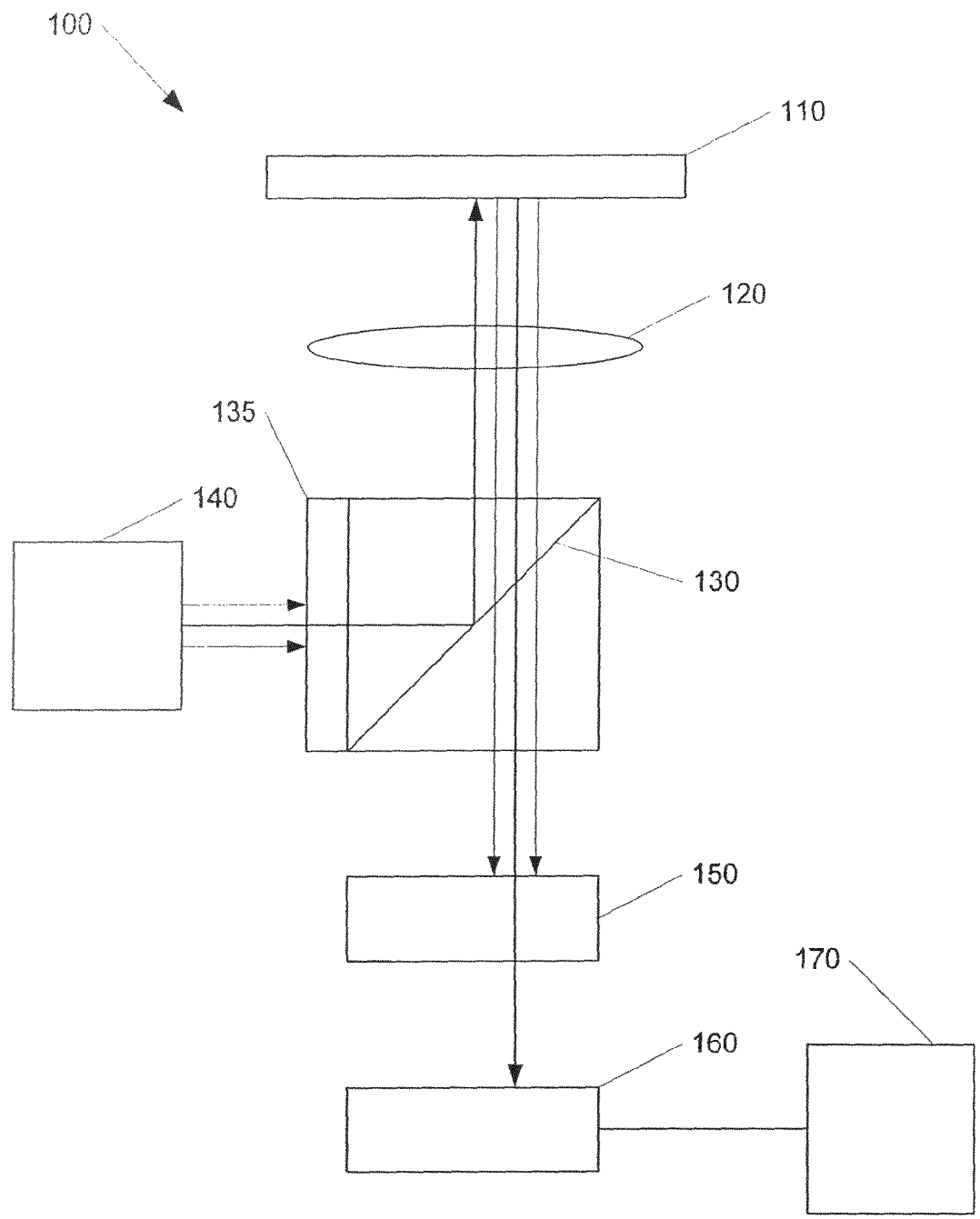
FIG. 1 is an imaging system equipped with an excitation interference filter, a mirror, and a tunable filter.
Figure 2:
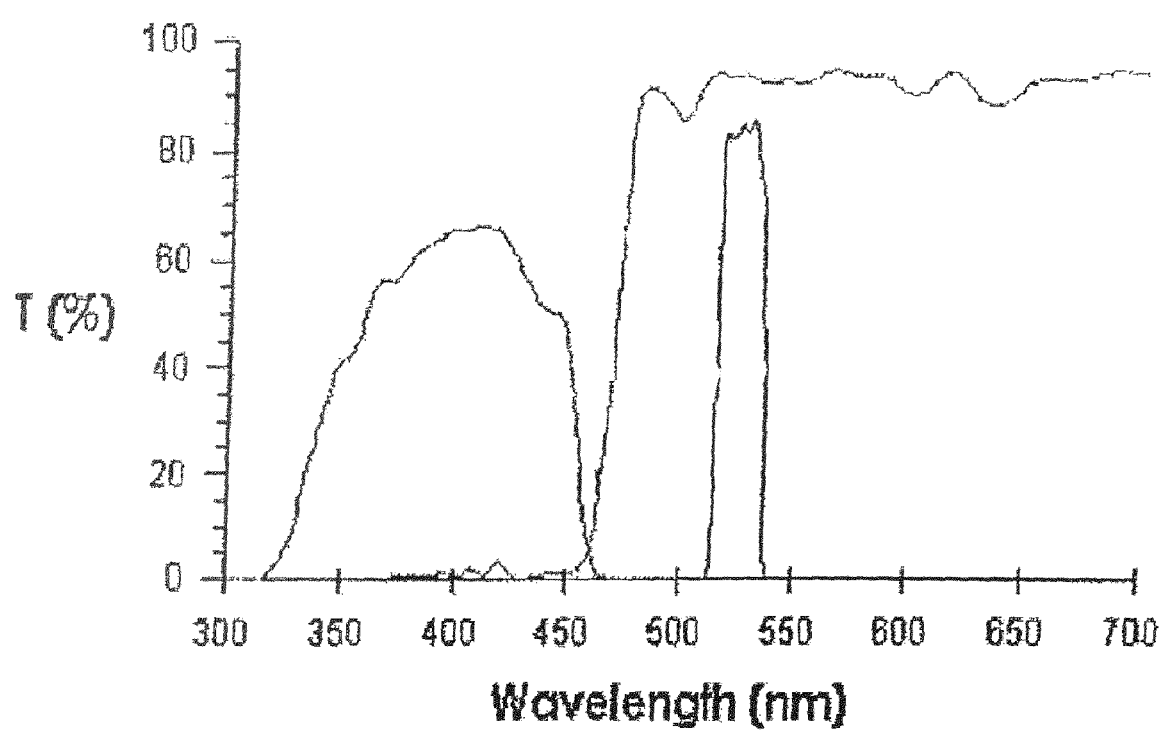
FIG. 2 is a graph of the transmittance spectrum of the interference filter and the mirror, and the emission spectrum of quantum dots.

FIG. 1 illustrates a block diagram of one exemplary system. In this embodiment, beads (e.g., microspheres) having target molecules immobilized thereon are analyzed using an automated epifluorescence microscope-based imaging system 100 to capture and measure the signals emitted from the beads at various emission wavelengths. (The optical system does not have to be an 'epi' systems. One could excite the sample with one optical system and collect emitted light with another optical system, as in the case of a darkfield illumination system.) Excitation radiation, such as UV light, is generated at a light source 140, for example, a mercury arc lamp. Examples of other suitable excitation radiation sources include, but are not limited to, visible light sources which emit, for example, blue light. The light is directed to an excitation filter 135 and then a dichroic mirror 130. The combination of the dichroic mirror 130 and the excitation filter 135 only allow the passage of near UV wavelengths (e.g., in the range of 360 nm to 460 nm) in this example. These wavelengths are desirably common excitation wavelengths for all QDs embedded in the microspheres. The light may be focused onto a sample 110 by a lens 120 to excite the QD-labeled microspheres. Back-scattered light generated by the excitation of the QD-labeled microspheres is collected by the lens 120 and passes again through the dichroic mirror 130. The back-scattered light then passes through a tunable filter 150, for example a VariSpec™ liquid crystal tunable band pass filter (Cambridge Research & Instrumentation Inc., Woburn, Mass., U.S. Pat. No. 5,689,317). The tunable band pass filter 150 in the emission optical path allows the passage of wavelengths in the range of, for example, 400 nm-700 nm and with bandwidth of, for example, 20 nm, and filters the signal coming from the sample 110 before it is sensed by a radiation detector, such as a cooled charge-coupled device 160 (CCD). An image captured by the cooled charge-coupled device 160 is then processed by an image analyzer 170.

Coding Scheme

Polystyrene microspheres in the HTS system may be embedded with multicolored QDs (see, for example, Han et al., "Quantum-dot-tagged microbeads for multiplexed optical coding of biomolecules," *Trends Biotechnol.* 20, 160-166 (2001); and U.S. Pat. No. 6,602,671) according to a 'binary' coding scheme in which each microsphere is identified by the combination of different colored QDs embedded in it. The color can either be present, '1' or absent, '0.' With the two easily distinguishable levels for each unique wavelength QD, a series of $2^N$ spectral codes may be generated from the series of 'N' wavelengths. The spectral code forms the identity of each microsphere, and microspheres with same colors of QDs embedded belong to the same class. A large number of distinguishable spectral codes allows for the simultaneous analysis of a large number of target molecules. Generally, these microbeads may be polymeric microbeads have cross-sectional diameters of, for example, about 100 μm or less. This includes microbeads having a cross-sectional diameter of about 10-100 nm, about 0.1-1.0 μm, about 1-10 μm, or about 10-100 μm.

Capture Probes and Target Molecules

Capture probes are molecules such as antibodies, ligands or polynucleotides which are immobilized on a solid support (e.g., microspheres) and react or hybridize specifically with target molecules such as antigens, receptors or polynucleotides present in the sample solution in order to immobilize targets on the support. Microspheres with the same spectral bar code are conjugated with the same capture probe and immobilize the same target molecules.

Assay System

Microspheres with different spectral codes and, thus, with different capture probes, may be mixed with an analyte-containing sample, such as a biological or immunological sample, that is then analyzed for the target molecules. This suspension mixture containing microspheres and target sample then may be added to microwells, where the target molecules react with or bind to the capture probes. The mixture of spectrally encoded microspheres that have undergone an assay is then allowed to sediment in the microwells, which have coverslip bottoms. Alternatively, the suspension array can be incubated in the test tubes where reaction or binding occurs, and then added to the microwells where assayed microspheres sediment down to their coverslip bottoms. In either case, specific binding of target molecules to capture probes results in a change in emission characteristics of the encoded microsphere conjugates.

Fluorescent Target Molecules

Target molecules can be labeled with different luminescent labels, such as fluorescent dyes or luminescent QDs (see, for example, U.S. Pat. No. 6,274,323), which can be excited by the same excitation radiation that is used to excite QDs labeling the microspheres. Preferably, the labels on the target molecules should have luminescence emission wavelengths lying between the greatest excitation wavelength of the excitation radiation and the smallest emission wavelength of the spectral emission from the QDs. However, the overlap of the label's emission spectrum with the emission from the QDs is desirably minimized. In an alternative embodiment, the target molecules may have emission wavelengths lying above the greatest emission wavelength of the spectral emission from the QDs. The target molecules may also have emission wavelengths that overlap with or are shorter than the shortest wavelengths of the excitation radiation.

In order to reduce the number of images needed for analysis, which would result in reduction of the processing time, the target molecules can be attached to labels having an excitation band as well as an emission band that falls within or overlaps with the excitation band of the QD labels. For example, Cascade Blue™, which has an excitation peak at 401 nm and an emission peak at 421 nm, may be a suitable dye. An image is acquired by tuning the tunable filter to 455 nm, where Cascade Blue™ has an emission around 53% of the maximum. The signal from the microspheres in this image is composed of back-scattered light and luminescence from the target molecules captured onto them. As a corollary, microspheres with no captured target molecules exhibit intensity corresponding to the back-scattered light only. Ideally, reflected light signals from microspheres with no captured target probes are identical for all the microspheres present in the image. Target luminescence from the assayed microspheres can be calculated by subtracting the reflected light signal from unassayed microspheres from the total signal from assayed microspheres provided that imaging conditions are kept the same. It is important that the dichroic mirror in the imaging system allow the passage of the emission from the labeled targets.

In the exemplary imaging system shown in FIG. 1, a dichroic mirror and an excitation interference filter may be used, both of which have some transmittance at 455 nm. This allows part of the light that passes through the filter to be reflected by the dichroic mirror to the sample and part of the light reflected from the sample to be transmitted through the dichroic mirror to be observed by CCD after it passes through the tunable filter. The system can acquire reflected light images with high signal to noise ratio at 455 nm with exposure times comparable to those required for acquiring the luminescence images at QD emission wavelengths indicating sufficient transmission. Thus, utilizing a dye with a considerable emission at 455 nm (e.g., Cascade Blue™ with emission 53% of the maximum, to label the target molecules would be ideal for the proposed strategy.

Image Analysis

An automated image analysis algorithm is also provided, based on a watershed scheme which can segment the clustered microspheres randomly scattered in the images (see, for example, Beucher, "The Watershed transformation applied to image segmentation," *Scanning Microscopy International* (1992); Beucher and Meyer, "The morphological approach to segmentation: The watershed transformation," In: Dougherty, E. R., editor, *Mathematical morphology in image processing*, New York, Basel, Hong Kong: Marchel Dekker, 433-482 (1993)). In a novel scheme, instead of localizing the microspheres, zones are identified corresponding to each microsphere in the reflected light image, which also contains target luminescence. A zone is an enclosed region formed by watershed lines and includes a microsphere and its neighboring background pixels. Ideally, each zone contains a single microsphere. In each zone, it is easy to differentiate microspheres from the background by simple intensity thresholding.

Zonal information from the image acquired at 455 nm is utilized to mark zones in the fluorescent images and simple thresholding is applied in each zone to demarcate the microspheres from the background. This zonal identification is better than identifying actual microspheres as sedimented microspheres might move slightly from their original positions (e.g., due to convection currents), thereby rendering localization schemes susceptible to errors. However, this might not be the case with microspheres covalently immobilized on planar surfaces or immobilized on membrane filters, where the localization scheme is sufficient. In order to make the method more accurate, luminescence from each microsphere may be recorded per unit pixel per unit exposure time. This eliminates errors due to differences in the size of microspheres, incorrect segmentation (e.g., removal of some pixels which actually belong to the microspheres) and the signal noise.

After the signal from the microspheres is read at different wavelengths, spectral codes are assigned on the basis of classification schemes such as clustering or discriminant analysis algorithms, the latter of which require training sets. The conjugated capture probe is identified by the spectral code of the microsphere, and, hence, the strength of fluorescent signal from the captured target molecules (as calculated above) quantifies the amount of corresponding target analyte present in the sample target solution based on a calibration chart.

In another embodiment, the imaging system and analysis methods can be implemented in highly multiplexed systems required for screening experiments, proteome analyses, and other applications involving complex biological samples where high throughput screening is required for the parallel identification of large sets of target proteins on arrays with thousands of specific capture molecules (see, for example, Stoll et al., "Protein microarray technology," *Frontiers in Bioscience* 7, c13-c32 (2002); Uetz et al. (2000); deWildt et al., "Antibody arrays for high-throughput screening of antibody-antigen interactions," *Nature Biotechnol.* 18, 989-994 (2000); Schaffitzel et al., "Ribosome display: an in vitro method for selection and evolution of antibodies from libraries," *J. Immunol, Methods* 231, 119-135 (1999). Since each candidate could potentially bind to thousands of proteins, $10^9$ to $10^{15}$ interactions may need to be examined. In addition, highly multiplexed protein array technologies may be important in future applications where a tiny array footprint is required to conserve rare samples. Array miniaturization may be important, for example, in forensic, archeological, and neonatal applications, as well as in research on endangered or extinct species.

For the purposes of this disclosure and unless otherwise specified, "a" or "an" means "one or more." All patents, applications, references and publications cited herein are incorporated by reference in their entirety to the same extent as if they were individually incorporated by reference.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

While the principles of this invention have been described in connection with specific embodiments, it should be understood clearly that these descriptions are made only by way of example and are not intended to limit the scope of the invention.

What is claimed is:

1. A method for identifying beads in a sample, wherein the beads are spectrally coded such that each bead has a characteristic spectral emission, the method comprising:

(a) directing excitation radiation onto the beads in the sample;
    (b) identifying the locations of the beads in the sample by detecting back-scattered radiation from the beads, wherein the back-scattered radiation passes through a tunable filter, which is tuned to an excitation wavelength of the excitation radiation, prior to being detected by a radiation detector; and
    (c) identifying the spectral code of each bead by detecting luminescence radiation emitted from each bead at a plurality of emission wavelengths, wherein the emitted luminescence radiation passes through the tunable filter, which is tuned sequentially to each of the plurality of emission wavelengths, prior to being detected by the radiation detector.

2. The method of claim 1, wherein the spectrally coded beads comprise polymeric microspheres embedded with quantum dots.

3. The method of claim 1, wherein at least some of the beads have target molecules immobilized thereon, the method further comprising detecting luminescence signal emitted from the target molecules.

4. The method of claim 3, wherein the target molecules are immobilized on the beads by specifically binding to capture probes on the beads, and further wherein beads having the same capture probes also have the same spectral code.

5. The method of claim 3, wherein the luminescence signal emitted from the target molecules is a fluorescence signal emitted by fluorescent labels on the target molecules.

6. The method of claim 3, wherein the luminescence signal emitted from the target molecules has emission wavelengths lying between the greatest excitation wavelength of the excitation radiation and the smallest emission wavelength of the spectral emission from the spectrally coded beads.

7. The method of claim 3, wherein the target molecules have an excitation band and an emission band that fall within or overlap with the excitation band of the spectrally coded beads.

8. The method of claim 7, further comprising subtracting the detected back-scattered radiation from the total signal due to back-scattering and luminescence emission from the beads.

9. The method of claim 3, further comprising quantifying the amount of each immobilized target molecule in the sample based on the strength of the luminescence signal emitted by the immobilized targets.

10. The method of claim 3 wherein the target molecules are selected from the group consisting of antibodies, antigens, ligands, receptors, and polynucleotides.

11. The method of claim 1, wherein the excitation radiation comprises ultraviolet light.

\* \* \* \* \*

UNITED STATES PATENT AND TRADEMARK OFFICE
CERTIFICATE OF CORRECTION

| | |
|---|---|
| PATENT NO. | : 7,764,361 B2 |
| APPLICATION NO. | : 11/829631 |
| DATED | : July 27, 2010 |
| INVENTOR(S) | : David M. Kelso and Abhishek Mathur |

It is certified that error appears in the above-identified patent and that said Letters Patent is hereby corrected as shown below:

Column 1, lines 14-17 should read --This invention was made with government support under Grant No. RO1EB001418 awarded by the National Institutes of Health (National Institute of Biomedical Imaging and Bioengineering). The government has certain rights in the invention.--

Signed and Sealed this

Fourteenth Day of September, 2010

David J. Kappos
*Director of the United States Patent and Trademark Office*